US008728510B1

(12) United States Patent
Roorda

(10) Patent No.: US 8,728,510 B1
(45) Date of Patent: May 20, 2014

(54) BIOCOMPATIBLE CARRIER CONTAINING A BIOADHESIVE MATERIAL

(75) Inventor: Wouter E. Roorda, Palo Alto, CA (US)

(73) Assignee: Advanced Cardiovascular Systems, Inc., Santa Clara, CA (US)

(*) Notice: Subject to any disclaimer, the term of this patent is extended or adjusted under 35 U.S.C. 154(b) by 490 days.

(21) Appl. No.: 10/098,686

(22) Filed: Mar. 15, 2002

(51) Int. Cl.
A61K 31/19 (2006.01)
A61K 38/12 (2006.01)
B05D 3/00 (2006.01)
B05D 1/00 (2006.01)

(52) U.S. Cl.
USPC ........................................ 424/423; 427/2.13

(58) Field of Classification Search
USPC ............. 424/493, 496–97, 499–501, 485–86, 424/488, 423; 427/2.13
See application file for complete search history.

(56) References Cited

U.S. PATENT DOCUMENTS

| | | | |
|---|---|---|---|
| 4,739,768 A | 4/1988 | Engelson | 128/658 |
| 5,091,205 A * | 2/1992 | Fan | 427/2.28 |
| 5,171,217 A | 12/1992 | March et al. | 604/53 |
| 5,295,962 A | 3/1994 | Crocker et al. | 604/101 |
| 5,324,261 A * | 6/1994 | Amundson et al. | 604/103.02 |
| 5,401,511 A | 3/1995 | Margalit | 424/450 |
| 5,472,704 A | 12/1995 | Santus et al. | 424/435 |
| 5,509,899 A * | 4/1996 | Fan et al. | 604/103.14 |
| 5,558,642 A | 9/1996 | Schweich, Jr. et al. | 604/96 |
| 5,576,025 A * | 11/1996 | Akiyama et al. | |
| 5,603,872 A | 2/1997 | Margalit | 264/4.3 |
| 5,607,694 A | 3/1997 | Marx | 424/450 |
| 5,611,775 A | 3/1997 | Machold et al. | 604/53 |
| 5,631,019 A | 5/1997 | Marx | 424/450 |
| 5,651,982 A | 7/1997 | Marx | 424/450 |
| 5,658,588 A | 8/1997 | Retzinger et al. | 424/450 |
| 5,723,269 A * | 3/1998 | Akagi et al. | 424/497 |
| 5,811,124 A | 9/1998 | Fernandez et al. | 424/489 |
| 5,817,343 A | 10/1998 | Burke | 424/489 |
| 5,846,561 A | 12/1998 | Margalit | 424/450 |
| 5,869,103 A | 2/1999 | Yeh et al. | 424/501 |
| 5,893,840 A | 4/1999 | Hull et al. | 604/96 |
| 5,912,015 A | 6/1999 | Bernstein et al. | 424/484 |
| 5,981,719 A | 11/1999 | Woiszwillo et al. | 530/410 |
| 6,123,965 A | 9/2000 | Jacob et al. | 424/489 |
| 6,287,588 B1 * | 9/2001 | Shih et al. | 424/426 |
| 6,447,835 B1 * | 9/2002 | Wang et al. | 427/2.24 |
| 6,800,073 B2 * | 10/2004 | Palasis et al. | 604/264 |
| 2001/0044651 A1 * | 11/2001 | Steinke et al. | 623/1.16 |
| 2002/0002353 A1 * | 1/2002 | Michal et al. | 604/265 |
| 2002/0055666 A1 * | 5/2002 | Hunter et al. | 600/1 |

OTHER PUBLICATIONS

Bakan, *Microcapsule Drug Delivery Systems*, Polymer Sci. & Tech., Polymers in Medicine & Surgery 8:213-35 (1975).
Bach, *Adherence of Albunex to an Apical Left Ventricular Thrombus*, J. Am. Soc. Echocardiogr. 12:761-2 (Sep. 1999).
Chary et al., *In Vitro and In Vivo Adhesion Testing of Mucoadhesive Drug Delivery Systems*, Drug Devel. and Ind. Pharm. 25(5):685-690 (May 1999).
Downing, *Venous Access—Specific Types Advantages and Disadvantages*, Seattle Treatment Education Project: STEP Perspective 4(3) (Oct. 1992), http://www.aegis.com/pubs/step/1992/STEP4301.html, printed Oct. 30, 2001.
Ghinea et al., *Cell Surface Chemistry of Arterial Endothelium and Blood Monocytes in the Normolipidemic Rabbit*, J. Submicrosc. Cytol. 19(2); 193-208 (1987).
Lehr, *Lectin-Mediated Drug Delivery: The Second Generation of Bioadhesives*, Journal of Controlled Release 65:19-29 (2000).
Le Ray et al., *Development of a "Continuous-Flow Adhesion Cell" for the Assessment of Hydrogel Adhesion*, Drug Devel. and Ind. Pharm. 25(8):897-904 (Aug. 1999).
Santos et al., *Correlation of Two Bioadhesion Assays: The Everted Sac Technique and the CAHN Microbalance*, Journal of Controlled Release 61:113-122 (Aug. 1999).
Shahidi et al., *Encapsulation of Food Ingredients*, Crit. Rev. in Food Sci. and Nutr. 33(6):501-547 (1993).
Thies, *Microcapsules as Drug Delivery Devices*, CRC Crit. Rev. in Biomed. Eng. 8(4):335-383 (1982).
Ueda et al., *Histochemical Analysis of Acidic Glycoconjugates in the Endothelium Lining of the Splenic Blood Vessels in the Rat*, Arch. Histol. Cytol. 59(4):389-397 (1996).
Villanueva et al., *Albumin Microbubble Adherence to Human Coronary Endothelium: Implications for Assessment of Endothelial Function Using Myocardial Contrast Echocardiography*, JACC 30(3): 689-93 (Sep. 1997).
Wilensky et al., *Direct Intraarterial Wall Injection of Microparticles Via a Catheter: A Potential Drug Delivery Strategy Following Angioplasty*, Amer. Heart J. 122(4):1136-1140 (Oct. 1991).
Wilensky et al., *Regional and Arterial Localization of Radioactive Microparticles After Local Delivery by Unsupported or Supported Porous Balloon Catheters*, Amer. Heart J. 129(5):852-859 (May 1995).
Carbopol® Polymers in Pharmaceuticals, http://www.pharma.bfgoodrich.com/products/carbopol.htm, printed Feb. 8, 2001.
Types of Devices, http://www.arcmesa.com/pdf/central_venous_cptco.../types_of_devices.htm, printed Oct. 30, 2001.
Carbopol® Powdered Polymers, product description, downloaded from: http://www.homecare.noveon.com/products/carbopol/carbopol.asp, Feb. 20, 2007, 2 pgs.
Cyanoacrylate, information from Wikipedia the free encyclopedia, downloaded from: http://en.wikipedia.org/wiki/Cyanoacrylate, Feb. 20, 2007, 4 pgs.

* cited by examiner

Primary Examiner — Janet Epps-Smith
Assistant Examiner — Courtney Brown
(74) Attorney, Agent, or Firm — Squire Sanders (US) LLP

(57) ABSTRACT

A biocompatible carrier for delivery of a therapeutic substance or an active agent is disclosed. The carrier contains a bioadhesive material allowing for increased residence time of the active agent at the treatment site.

6 Claims, No Drawings

BIOCOMPATIBLE CARRIER CONTAINING A BIOADHESIVE MATERIAL

BACKGROUND OF THE INVENTION

1. Field of the Invention

This invention relates to a biocompatible carrier containing an active ingredient for introducing the active ingredient to a target cell population, such as smooth muscle cells, requiring modulation to ameliorate a diseased state such as restenosis. More particularly, the invention is directed to a polymeric matrix that contains a bioadhesive formulation for specific or non-specific binding to a biological target.

2. Description of the Background

Systemic administration of a drug for the treatment of a disease, such as a tumor or vascular restenosis, can be accomplished by administering large quantities of the drug orally or parenterally. Large quantities or dosages are needed to provide an efficacious concentration of the drug to the treatment site. Because of the necessity to use large quantities of the drug, systemic administration can produce toxic side effects for the patient, and can adversely affect healthy tissues which need not be exposed to the drug. Local delivery of the drug, under many circumstances, such as for the treatment of restenosis, is the preferred method of administration. In comparison to systemic administration, smaller total levels of medication can be administered locally, but are concentrated at a specific site. Local delivery, thus, produces fewer side effects and achieves more favorable results. Local delivery can be accomplished by a variety of methods, such as with the use of polymeric particles imbedded with a drug that are placed via a catheter in the area in need of treatment. The drugs can slowly elute from the polymer or are released as the polymer degrades or absorbs into the environment. One drawback of local delivery includes the short residence time of the drug at the targeted location. The absorption of drugs into and through the tissue of the target area is often inadequate for the effective treatment of the patient. Accordingly, it is desirable to provide an improved carrier composition that provides for a more effective localized delivery of a drug.

SUMMARY

In accordance with one embodiment of the present invention a composition for introducing a therapeutic compound to a vessel is provided, comprising a carrier, a therapeutic compound contained in the carrier and a bioadhesive material contained in or coated on the carrier for attaching the carrier to a target area of the vessel. The carrier can, for example, be made from a biodegradable or bioabsorbable polymer.

In one embodiment, the bioadhesive material binds non-specifically to a biological molecule in a tissue. The nonspecific bioadhesive material can be, for example, CARBOPOL® polymers, homopolymers and copolymers, Carbopol-poloxamer gels, hydroxypropylmethylcellulose, sodium carboxymethyl cellulose, Guar gum, polyvinyl pyrrolidone, chitosan, polyacrylic acid, hydroxypropyl cellulose, polycarbophil, sodium starch glycolate, alginate, mixtures, copolymers, and grafts thereof.

In accordance with another embodiment, the bioadhesive material binds specifically to a biological molecule in a tissue. The specific bioadhesive material can bind to a component of an extracellular matrix or a receptor molecule on a cell. The receptor molecule can be a cell adhesion molecule, CD14, beta2 integrin, or glycoprotein IIb/IIIa platelet fibrinogen receptor. The cell adhesion molecule can be vascular cell adhesion molecule-1 (VCAM-1), inflammatory cell adhesion molecule-1 (ICAM-1), endothelial cell adhesion molecule-1 (ECAM-1), or platelet endothelial cell adhesion molecule-1 (PCAM-1). The specific bioadhesive material can be a lectin, a ligand for cell adhesion molecule, an antibody for cell adhesion molecule, a ligand for glycoprotein IIb/IIIa platelet fibrinogen receptor, ReoPro, Integrelin, or albumin. In one embodiment, the therapeutic agent can be for reducing, delaying or eliminating restenosis of a blood vessel.

In accordance with another embodiment of the invention, a method of reducing, delaying or eliminating restenosis of a blood vessel is provided, comprising depositing into a designated region of the blood vessel a composition which comprises a therapeutic agent in a polymeric carrier, and a bioadhesive material. The polymeric carrier can be a particle, such as a micro or nanoparticle coated with or containing the bioadhesive material. The bioadhesive material can be capable of binding specifically to vascular smooth muscle cells. The bioadhesive material can bind non-specifically or specifically to a biological molecule in the blood vessel.

In accordance with another embodiment of the invention, a method for delivering a therapeutic agent to a lesion defining an occlusion in a blood vessel is provided, comprising: inserting a surgical instrument in close proximity to the lesion in the blood vessel; and injecting particles from the surgical instrument, the particles including a therapeutic substance for the treatment of the lesion and a bioadhesive material for binding the particles to the lesion or in an area in close proximity to the lesion.

DETAILED DESCRIPTION

As used herein, "abnormal" or "inappropriate" proliferation means division, growth or migration of cells occurring more rapidly or to a significantly greater extent than which typically occurs in a normally functioning cell of the same type, i.e., hyperproliferation.

As used herein, "analogs" or "derivatives" refer to a structural or functional variation of a therapeutic compound or an active agent, including fragments, derivatizations, or other chemical modifications, so long as the compound retains its characteristic biological activity.

As used herein, "bioadhesive" or "bio-adhesive" composition, formulation, material and the like refer to a naturally occurring or synthetic compound that adheres, binds or interacts with a biological tissue, including a lumen wall such as a vascular wall. The bioadhesive used with the carrier of the invention results in prolonging the residence time of the therapeutic substance at the site of contact. It is understood that the bioadhesive material may be found anywhere on or in the carrier. For example, the bioadhesive material may be incorporated in the core, as a layer covering the core, coated on the carrier, or within any part of the carrier.

As used herein, "core" refers to a portion of the carrier that contains an active ingredient or a therapeutic compound. The core may also contain a bioadhesive material. The core can be made from any suitable material, such as a polymeric material, either synthetically or naturally derived material. The bioadhesive can be combined with the polymeric matrix and the active ingredient in either a blended fashion or by covalent linkages, or by employing a variety of types of interactive forces.

As used herein, "early stage cancer" refers to the early aspect of cancer progression, such as local invasion and micrometastasis.

As used herein, "inhibiting" cellular activity means reducing, delaying or eliminating smooth muscle cell hyperplasia, restenosis, and vascular occlusions, particularly following biologically or mechanically mediated vascular injury or trauma or under conditions that would predispose a mammal to suffer such a vascular injury or trauma. The invention is also directed to treating or inhibiting early stage cancer and any other disease for which administration of a therapeutic compound is useful. As used herein, the term "reducing" means decreasing neoplastic proliferation of cells, in particular, vascular smooth muscle cells. In addition, "reducing" also means decreasing the level of a disease state. "Delaying" means retarding the progression of a hyper-proliferative disease or neoplastic proliferation, or any other disease state, as observed for example, by histological or angiographic examination. The effects of treating, reducing, delaying, or eliminating smooth muscle cell hyperplasia, restenosis vascular occlusions, neoplastic proliferation or any other disease state, may be determined by methods known to one of ordinary skill in the art, including, but not limited to, angiography, ultrasonic evaluation, fluoroscopy imaging, fiber optic visualization, or biopsy and histology.

Biologically mediated vascular injury includes, but is not limited to injury caused by or attributed to autoimmune disorders, alloimmune related disorders, infectious disorders including endotoxins and herpes viruses such as cytomegalovirus, metabolic disorders such as atherosclerosis, and vascular injury resulting from hypothermia, irradiation and cancer. Mechanical mediated vascular injury includes, but is not limited to vascular injury caused by catheterization procedures or vascular scraping procedures such as percutaneous transluminal coronary angioplasty, vascular surgery, stent placement, transplantation surgery, laser treatment, and other invasive procedures which disrupted the integrity of the vascular intima or endothelium. The active ingredient or therapeutic compound used with the practice of the invention is not restricted in use for therapy following vascular injury or trauma; rather, the usefulness of the active ingredient will also be determined by the ingredient's ability to inhibit cellular activity of smooth muscle cells or inhibit various diseases including early stage cancer.

As used herein, "neoplastic proliferation" means new and abnormal growth or proliferation of tissue, which may be benign or cancerous.

As used herein, a "carrier" refers to a substance that contains a therapeutic compound in combination with a bioadhesive material. The carrier can be, for example, a particle of any suitable size such as in the range of a microparticle or nanoparticle. The carrier includes the core for the sustained release of the therapeutic compound.

As used herein, "proliferation" of smooth muscle cells means increase in cell number.

As used herein, "smooth muscle cells" include those cells derived from the medial and adventitia layers of the vessel which proliferate in intimal hyperplastic vascular sites following vascular trauma or injury. Under light microscopic examination, characteristics of smooth muscle cells include a histological morphology of a spindle shape with an oblong nucleus located centrally in the cell with nucleoli present and myofibrils in the sarcoplasm. Under electron microscopic examination, smooth muscle cells have long slender mitochondria in the juxtanuclear sarcoplasm, a few tubular elements of granular endoplasmic reticulum, and numerous clusters of free ribosomes. A small Golgi complex may also be located near one pole of the nucleus.

As used herein, "substantially non-immunogenic" means that the compound does not elicit a significant immune response to be detrimental to human health.

The core may be fully or partially surrounded by a layer of bio-adhesive material. Alternatively, the bioadhesive material may be combined with the core. In the case where the bioadhesive material is supplied in a layer that surrounds the core, the size of the particle depends on the bio-adhesive material chosen. The particle should be large enough so that the particle adheres to the tissue. However, the particle should not be so thick as to make the size of the particle larger than necessary. Additionally, the bioadhesive layer may affect the release profile of the therapeutic substance, and therefore the thickness of the particle should not hinder or adversely alter the desired release profile of the therapeutic substance.

In addition to having adhesive properties, suitable bioadhesive materials should be bio-compatible, that is non-toxic, non-inflammatory, and substantially non-immunogenic in the amounts employed. When the carrier is to be used within the vascular system, the bio-adhesive material should also be hemo-compatible.

Bio-adhesive materials can either have non-specific or specific binding properties. Bio-adhesive materials with non-specific binding properties will adhere generally to the cells and the components of the extracellular matrix that form the tissue at the treatment site, through, for example, charge interactions. Examples of bio-adhesive material with non-specific binding properties include, but are not limited to, CARBOPOL® (BF Goodrich Performance Materials, Cleveland, Ohio) polymers, homopolymers, copolymers, and the like. The CARBOPOL® polymers include high molecular weight, crosslinked, acrylic acid-based polymers. CARBOPOL® homopolymers include polymers of acrylic acid crosslinked with allyl sucrose or allylpentaerythritol. CARBOPOL® copolymers include polymers of acrylic acid, modified by long chain ($C_{10}$-$C_{30}$) alkyl acrylates, and crosslinked with allylpentaerythritol. Other examples include, Carbopol-poloxamer gels, hydroxypropylmethylcellulose, sodium carboxymethyl cellulose, Guar gum, polyvinyl pyrrolidone, chitosan, polyacrylic acid, hydroxypropyl cellulose, polycarbophil, sodium starch glycolate, alginate, and their mixtures and/or copolymers, as well as mixtures, copolymers or graft constructs with polyethylene glycol.

Bio-adhesive materials with specific binding properties adhere to tissue through specific intermolecular interactions with molecules exposed on the surface of the cells and matrix of the tissue at the treatment site. The cells at the treatment site may be, for example, the layer of endothelial cells that line the vascular lumen, or other cells, such as inflammatory cells, that have been deposited on the vascular lumen at, for instance, the site of a vascular lesion. Examples of bio-adhesive materials with specific binding properties include, but are not limited to, lectins, ligands and antibodies to receptor proteins such as cell adhesion molecules and integrins, and albumin.

The particular bio-adhesive material will depend on the intended use of the carrier, and, in particular, the characteristics of the treatment site to which the carrier needs to adhere. For example, in relatively healthy, undamaged blood vessels, the layer of endothelial cells that line the blood vessel, known as the endothelium, have a large number of positively charged molecular groups in a non-specific distribution exposed at the cell surface. Thus, if the target treatment site for the particle is an undamaged blood vessel, a negatively charged bio-adhesive material, for example, sodium carboxymethyl cellulose, may be selected.

Alternatively, the treatment site may be a place where the endothelium is damaged by biologically and/or mechanically mediated vascular injury. If there is substantial damage to the endothelium at the desired treatment site, with exposure of the underlying extra-cellular matrix, known as the basal lamina, negatively charged molecules such as heparan sulfate and chondroitin sulfate are exposed. Thus, a bio-adhesive material that is positively charged, such as a chitosan-based material, may be chosen for the particle when the target treatment site is a damaged blood vessel.

If a more specific and directed attachment of the particle to a particular treatment site is desired, a bio-adhesive material with specific binding properties can be chosen for use in the carrier composition. For instance, a bio-adhesive material that binds to molecules exposed only on tissues in specific regions of the body can be used, thus directing the particle to bind to those tissues. Alternatively, if the treatment site is a region of tissue that is diseased or injured, the particle can be targeted to the treatment site by using a bio-adhesive material that binds to molecules that are exposed on that region of tissue due to the disease or injury.

Many components on cell surfaces, particularly those of the arterial endothelium, are glycosylated and have exposed sugar moieties. Lectins are proteins or glyco-protein conjugates that bind to sugar moieties, and therefore, lectins will bind to glycosylated cell surface. If the target treatment site is the heavily glycosylated endothelium of an artery, lectins can be used as a bio-adhesive material that will adhere to the arterial wall. Lectins are also advantageous because they are generally non-immunogenic. Examples of lectins include, but are not limited to, *Lycopersicon eculantum* agglutinin, wheat germ agglutinin, *Urtica dioica* agglutinin, peanut agglutinin, tomato lectin, and *Ulex europaeus* isoagglutinin.

Receptor proteins known as adhesion molecules are also exposed on the surface of cells. Adhesion molecules mediate cell-cell binding by specifically recognizing and binding to molecules on the surface of other cells. Thus, ligands or antibodies that bind to adhesion molecules exposed on the surface of cells at a particular treatment site can be used as a specific bio-adhesive material to a treatment site.

For example, adhesion molecules exposed on the endothelium of blood vessels function as recognition and attachment sites for cells circulating in the blood, such as neutrophils, monocytes, and macrophages. Examples of such adhesion molecules include vascular cell adhesion molecule-1 (VCAM-1), inflammatory cell adhesion molecule-1 (ICAM-1), endothelial cell adhesion molecule-1 (ECAM-1), and platelet endothelial cell adhesion molecule-1 (PCAM-1). These adhesion molecules are upregulated and appear in greater numbers at sites where blood vessels are inflamed, a condition that often occurs in association with atherosclerotic plaque. Therefore, if the desired treatment site is an inflamed blood vessel, the polymeric carrier composition may contain ligands and antibodies to the adhesion molecules to adhere to the desired treatment site. Additionally, the circulating cells, such as neutrophils, that bind to the adhesion molecules present at sites of inflammation have surface molecules that are recognized and bound by the adhesion molecules. Examples of these surface molecules include CD14 and beta-2 integrin, which can be used as a bioadhesive compound in the present invention. An additional benefit of adhering the carrier to the adhesion molecules is that the particles may then prevent cells circulating in the blood stream from binding to the inflamed site, hindering the progression of inflammation that leads to further arterial damage.

The inflammatory cells themselves, for example neutrophils or monocytes, that are present in inflamed blood vessels have molecules on their surface that can also provide specific attachment sites for bio-adhesive material.

Damage to a blood vessel can also cause thrombus formation, which results from the activation and aggregation of platelets at the damaged site. Thrombus formation involves the cell surface glycoprotein IIb/IIIa platelet fibrinogen receptor. This receptor protein is exposed at the site of the damaged blood vessel as well as on the surface of the platelets that are deposited in the damaged site. Thus, molecules that bind to this receptor can be used as a bio-adhesive material that will bind the particle to a damaged vascular site.

Examples of molecules that bind to the glycoprotein IIb/IIIa platelet fibrinogen receptor include fibrinogen, which is the natural ligand for the receptor, abciximab (e.g., REOPRO® from Eli Lilly and Company, Indianapolis, Ind.), which is an antibody to the receptor, and eptifibatide (e.g., Integrilin from COR Therapeutics, Inc., San Francisco, Calif. and Key Pharmaceuticals, Inc., Kenilworth, N.J.), which is a synthetic ligand for the receptor. Ligands that contain RGD (Arg-Gly-Asp) amino acid sequence generally bind to leukocyte-directed integrins which may be present at the damaged vascular site. In addition to bio-adhesive properties, these ligands and antibodies, which were developed to reduce platelet aggregation and thrombosis, may have therapeutic effects at the treatment site and act as specific adhesive agents to injured vessel walls.

Another molecule that binds to disrupted endothelial cells is albumin. Since atherosclerotic processes, as well as vascular intervention procedures have a tendency to disrupt endothelium, using albumin in a bio-adhesive layer of the polymeric carrier may bind the particle to such an atherosclerotic treatment site. Additionally, albumin can be used as a carrier material, and thus the particle may be made entirely of albumin and the therapeutic substance.

In one embodiment, an outer layer of the carrier may be made from a mixture of bio-adhesive materials. For instance, a bio-adhesive material having non-specific binding properties may be mixed with a bio-adhesive material having specific binding properties. Such a mixture may improve adhesion of the carrier particle to a particular treatment site by using, for example, both non-specific charge interactions and specific intermolecular interactions between the bio-adhesive materials and the tissue at the treatment site.

The bio-adhesive material can be combined with the core or the carrier through physical interactions between the bio-adhesive material and the material of the core and/or carrier. These interactions include, for example, polymer chain entanglement and hydrogen bonding. As an alternative, covalent attachment can also be used to secure the bio-adhesive material to the carrier material. Covalent attachment, which is typically stronger than physical interactions, may be especially useful for attaching smaller bioadhesive molecules to the carrier.

The carrier can be delivered using any apparatus or technique. For example, the particles may be applied to a target tissue using a percutaneous site-specific delivery device, an example of which is a delivery catheter. Such a delivery catheter may be used to deliver particles to treatment sites within, for example, the vascular system, urethra, bile duct, or lymph vessels.

When a balloon catheter is used, the pressure inside the inflated balloon will cause the wall of the balloon to press against the tissue. The bioadhesive composition should have greater affinity for the vessel wall than the catheter. The carrier, which is located between the balloon wall and the tissue, will thus be forced against the tissue. This force on the carrier actually increases the amount of contact area between the bio-adhesive composition on the carrier and the cells and matrix that form the tissue of the lumen. The force of the balloon also increases the length of time the carrier is in contact with the tissue. The increased contact area and time enhances the adhesion of the carrier to the treatment site. An example of a balloon catheter that may be particularly useful is infusion balloon catheter, wherein the bio-adhesive composition may be coated on the outside of the catheter, and/or the active ingredients may be combined with a biodegradable polymer and a bio-adhesive composition to form particles, in which the particles are injected and are released through the holes on the side of the catheter.

In the present application, the phrase "active ingredient" may be used interchangeably with "therapeutic compound," "active agent," "drug," "bioactive compound" and the like. In one embodiment of the invention, the active ingredient may be contained in a single layer of a polymer for the carrier. Alternatively, the active ingredient or a combination of active ingredients may be contained in a plurality of layers of the same or a variety of polymers. Polymers free from the active ingredient can also be used as a diffusion barrier. In one embodiment, the bioadhesive compound may be combined with or included on the outermost layer of the carrier. Alternatively, the bioadhesive compound may be contained in any of the layers, depending on the level of control of binding and release of the active ingredient that is desired.

The active ingredient can be for inhibiting the activity of a particular target cell population, such as vascular smooth muscle cells. More particularly, in one embodiment, the active ingredient can be for inhibiting, delaying, or eliminating abnormal or inappropriate smooth muscle cell migration and/or proliferation, restenosis, or early stage cancer. The usefulness of the active ingredient should not, however, be limited to inhibition of a particular cellular activity. The active ingredient's usefulness should be measured by the ingredient's ability to have a therapeutic or prophylactic effect. Representative examples of the active ingredients or agents that can be used include antiproliferative substances such as actinomycin D, or derivatives and analogs thereof (manufactured by Sigma-Aldrich 1001 West Saint Paul Avenue, Milwaukee, Wis. 53233; or COSMEGEN available from Merck). Synonyms of actinomycin D include dactinomycin, actinomycin IV, actinomycin I, actinomycin X1, and actinomycin C1. The active agent can also fall under the genus of antineoplastic, antiinflammatory, antiplatelet, anticoagulant, antifibrin, antithrombin, antimitotic, antibiotic, antiallergic and antioxidant substances. Examples of such antineoplastics and/or antimitotics include paclitaxel (e.g. TAXOL® by Bristol-Myers Squibb Co., Stamford, Conn.), docetaxel (e.g. Taxotere®, from Aventis S.A., Frankfurt, Germany) methotrexate, azathioprine, vincristine, vinblastine, fluorouracil, doxorubicin hydrochloride (e.g. Adriamycin® from Pharmacia & Upjohn, Peapack N.J.), and mitomycin (e.g. Mutamycin® from Bristol-Myers Squibb Co., Stamford, Conn.) Examples of such antiplatelets, anticoagulants, antifibrin, and antithrombins include sodium heparin, low molecular weight heparins, heparinoids, hirudin, argatroban, forskolin, vapiprost, prostacyclin and prostacyclin analogues, dextran, D-phe-pro-arg-chloromethylketone (synthetic antithrombin), dipyridamole, glycoprotein IIb/IIIa platelet membrane receptor antagonist antibody, recombinant hirudin, and thrombin inhibitors such as Angiomax™ (bivalirudin, Biogen, Inc., Cambridge, Mass.) Examples of such cytostatic or antiproliferative agents include angiopeptin, angiotensin converting enzyme inhibitors such as captopril (e.g. Capoten® and Capozide® from Bristol-Myers Squibb Co., Stamford, Conn.), cilazapril or lisinopril (e.g. Prinivil® and Prinzide® from Merck & Co., Inc., Whitehouse Station, N.J.); calcium channel blockers (such as nifedipine), colchicine, fibroblast growth factor (FGF) antagonists, fish oil (omega 3-fatty acid), histamine antagonists, lovastatin (an inhibitor of HMG-CoA reductase, a cholesterol lowering drug, brand name Mevacor® from Merck & Co., Inc., Whitehouse Station, N.J.), monoclonal antibodies (such as those specific for Platelet-Derived Growth Factor (PDGF) receptors), nitroprusside, phosphodiesterase inhibitors, prostaglandin inhibitors, suramin, serotonin blockers, steroids, thioprotease inhibitors, triazolopyrimidine (a PDGF antagonist), and nitric oxide. An example of an antiallergic agent is permirolast potassium. Other therapeutic substances or agents which may be appropriate include alpha-interferon, genetically engineered epithelial cells, rapamycin, dexamethasone and derivatives thereof. While the preventative and treatment properties of the foregoing therapeutic substances or agents are well-known to those of ordinary skill in the art, the substances or agents are provided by way of example and are not meant to be limiting. Other therapeutic substances are equally applicable for use with the disclosed methods and compositions.

The dosage or concentration of the active ingredient required to produce a favorable therapeutic effect should be less than the level at which the active ingredient produces toxic effects and greater than the level at which non-therapeutic results are obtained. The dosage or concentration of the active ingredient required to inhibit the desired cellular activity of the vascular region can depend upon factors such as the particular circumstances of the patient; the nature of the trauma; the nature of the therapy desired; the time over which the ingredient administered resides at the vascular site; and if other therapeutic agents are employed, the nature and type of the substance or combination of substances. Therapeutic effective dosages can be determined empirically, for example by infusing vessels from suitable animal model systems and using immunohistochemical, fluorescent or electron microscopy methods to detect the agent and its effects, or by conducting suitable in vitro studies. Standard pharmacological test procedures to determine dosages are understood by one of ordinary skill in the art.

The carrier composition can be made using any conventional and well-known processes known to one of ordinary skill in the art. These processes include, but are not limited to, solvent evaporation, hot melt microencapsulation, emulsification, phase separation, film casting, molding, spray drying, and coextrusion. The particular process chosen for creating the carrier will depend on the material used and the desired properties of the particle, such as the size of the particle and the desired release profile of the therapeutic substance. Additionally, the process chosen should be compatible with the therapeutic substance to be suspended or encapsulated with the polymer matrix, so that processing the conditions, e.g., temperatures or solvents, do not adversely alter the therapeutic substance.

Choosing a process method that does not adversely affect the therapeutic substance is particularly important in the case of proteinaceous therapeutic substances, as well as proteinaceous bioadhesive compositions, which are susceptible to denaturation and, for the therapeutic substance, loss of efficacy, and for the bioadhesive composition, loss of or reduced level of adherence to the target tissue location. In general, processes with low temperatures and mild solvents (no strong organic or acidic solvents) work best with proteinaceous therapeutic substances, but the process used will depend on the particular requirements of the individual protein.

In one embodiment of the invention, the carrier comprising a bioadhesive compound may be either injected from a surgical instrument, such as a catheter or a syringe, and/or the carrier may be coated on to the surgical instrument, so long as the bioadhesive composition has greater adhesiveness to the vessel wall than the surgical instrument. The underlying structure of the surgical instrument can be virtually any design, so long as the object has the capability of entering a vessel to inject and/or withdraw fluid from the vessel. Some examples of various types of surgical instruments are infusion catheters, tunneled catheters, non-tunneled catheters, catheters using implanted port, midline peripheral catheters, central catheters, as well as syringes that use steel needles or round flexible tubes, and other devices that can be, for example, administered percutaneously and into the blood vessel.

Suitable polymers for carrier material include, but are not limited to, biodegradable or bioabsorbable polymers, biomolecules, and biostable polymers. A biodegradable or bioabsorbable polymer breaks down in the body and is not present sufficiently long after delivery to cause an adverse local response. Bioabsorbable polymers are gradually absorbed or eliminated by the body by hydrolysis, metabolic process, bulk, or surface erosion. Examples of bioabsorbable materials include, but are not limited to, polycaprolactone (PCL), poly-D, L-lactic acid (DL-PLA), poly-L-lactic acid (L-PLA), poly(lactide-co-glycolide), poly(hydroxybutyrate), poly(hydroxybutyrate-co-valerate), polyorthoesters, polyanhydrides, poly(glycolic acid), poly(glycolic acid-cotrimethylene carbonate), polyphosphoesters, polyphosphoester urethane, poly (amino acids), polyamides, polyacetals, cyanoacrylates, poly(trimethylene carbonate), poly(iminocarbonate), copoly(ether-esters), polyalkylene oxalates, polyphosphazenes, polyiminocarbonates, and aliphatic polycarbonates.

Biomolecules such as fibrin, fibrinogen, cellulose, starch, albumin, glycosaminoglycans and collagen are typically also suitable. In another embodiment of the invention, heparin or heparin having hydrophobic counter ions (e.g. DURAFLO®) can be used.

A biostable polymer does not break down in the body, and thus a biostable polymer is present in the body for a substantial amount of time after delivery unless some modification is made to allow the polymer to break down. Examples of biostable polymers include, but are not limited to, Parylene, ParyLAST, polyurethane, segmented polyurethanes such as Biospan, polyethylene, polyethlyene terephthalate, ethylene vinyl acetate, silicone, ethylene vinyl alcohol copolymer, and polyethylene oxide. In addition, the carrier material may be a combination or blend of any polymeric material.

The carrier material and the therapeutic substance should be mutually compatible, such that the characteristics, effectiveness, and physical structure of the therapeutic substance and the carrier material are not adversely altered by the presence of the other. The number, type, and concentration of the therapeutic substance or substances is treatment-specific.

Numerous other uses can be envisioned for the carrier particle, particularly when delivered via a balloon catheter. For example, the particles that are coated with an outer layer of heparan sulfate, which, as described above adheres to basal lamina exposed after damage to the endothelium, may be delivered during and/or after a PCTA procedure. Such a polymeric particle may contain antithrombotic therapeutic substances, such as vapiprost and low molecular weight heparin, to prevent thrombus formation at the PCTA site. The release profile of such particles may be designed to quickly release the antithrombotic, because thrombosis tends to occur rapidly after injury. If it is determined that restenosis may occur, and it is believed the initial damage has begun to heal, the PCTA procedure may be followed by another PCTA procedure. In one useful embodiment, the particles used in the second procedure may be coated with an outer layer containing a lectin, such as tomato lectins, which will adhere to the healing cells at the treatment site. Such a particle may release, for instance, an anti-proliferative therapeutic substance, such as rapamycin, and be designed for slow, long-term release of the therapeutic substance, to prevent excess cell proliferation at the treatment site as it heals.

While particular embodiments of the present invention have been shown and described, it will be obvious to those skilled in the art that changes and modifications can be made without departing from this invention in its broader aspects and, therefore, the appended claims are to encompass within their scope all such changes and modifications as fall within the true spirit and scope of this invention.

What is claimed is:

1. A coating composition for introducing a therapeutic compound to a blood vessel, the composition comprising:
   a therapeutic compound;
   a carrier made from a carrier material for delivery of the therapeutic compound, wherein the carrier material is selected from the group consisting of polyphosphoesters, and
   a bioadhesive material contained in the carrier,
   wherein the carrier material and the bioadhesive material are a blood compatible formulation,
   the bioadhesive material comprises sodium starch glycolate,
   and
   the composition is coated on the outside of a balloon catheter.

2. The coating composition according to claim 1, wherein the therapeutic compound is selected from those that ameliorate restenosis of a blood vessel.

3. The coating composition according to claim 1, wherein the coating composition has a greater affinity for the blood vessel wall than the catheter.

4. The coating composition according to claim 1, wherein the therapeutic substance is a member of at least one genus selected from the group consisting of antineoplastic, antiinflammatory, antiplatelet, anticoagulant, antifibrin, antithrombin, antimitotic, antibiotic, antiallergic, and antioxidant substances.

5. The coating composition according to claim 1, wherein the therapeutic substance is selected from the group consisting of actinomycin D, dactinomycin, actinomycin IV, actinomycin I, actinomycin X1, actinomycin C, paclitaxel, docetaxel, methotrexate, azathioprine, vincristine, vinblastine, fluorouracil, doxorubicin hydrochloride, mitomycin, sodium heparin, hirudin, argatroban, forskolin, vapiprost, prostacyclin, dextran, D-phe-pro-arg-chloromethylketone (synthetic antithrombin), dipyridamole, glycoprotein IIb/IIIa platelet membrane receptor antagonist antibody, bivalirudin, angiopeptin, captopril, cilazapril, lisinopril, nifedipine, colchicine, lovastatin, nitroprusside, suramin, triazolopyrimidine, nitric oxide, permirolast potassium, rapamycin, dexamethasone, and combinations thereof.

6. The coating composition according to claim 1, wherein the therapeutic substance comprises a member of the group consisting of paclitaxel, docetaxel, sodium heparin, rapamycin, and dexamethasone.

* * * * *